US005727546A

United States Patent [19]
Clarke et al.

[11] Patent Number: 5,727,546
[45] Date of Patent: Mar. 17, 1998

[54] POWDER INHALER WITH BREATH FLOW REGULATION VALVE

[75] Inventors: Alastair Robert Clarke, Shepshed; Clive Sleath, Mountsorrel; Michael Trevor Shepherd, Quorn, all of United Kingdom

[73] Assignee: Fisons plc, Suffolk, United Kingdom

[21] Appl. No.: 596,311

[22] PCT Filed: Aug. 18, 1994

[86] PCT No.: PCT/GB94/01812

§ 371 Date: Jul. 17, 1996

§ 102(e) Date: Jul. 17, 1996

[87] PCT Pub. No.: WO95/05208

PCT Pub. Date: Feb. 23, 1995

[30] Foreign Application Priority Data

Aug. 18, 1993 [GB] United Kingdom ............... 9317196
Aug. 18, 1993 [GB] United Kingdom ............... 9317197
Aug. 18, 1993 [GB] United Kingdom ............... 9317198

[51] Int. Cl.$^6$ ................ A61M 15/00; A61M 16/00; B05D 7/14; B65D 83/06
[52] U.S. Cl. ............... 128/203.15; 128/203.24; 128/203.23; 128/205.24
[58] Field of Search ............. 128/200.24, 203.12, 128/203.15, 203.19–203.25, 205.24

[56] References Cited

U.S. PATENT DOCUMENTS

| 3,669,113 | 6/1972 | Altounyan et al. ............. 128/203.15 |
| 3,874,378 | 4/1975 | Isaacson et al. |
| 3,970,105 | 7/1976 | Pelton et al. |
| 4,092,999 | 6/1978 | Rubrich. |
| 4,259,951 | 4/1981 | Chernack et al. |
| 4,534,343 | 8/1985 | Brisson. |
| 4,819,629 | 4/1989 | Jonson. |
| 5,161,524 | 11/1992 | Evans. |
| 5,349,947 | 9/1994 | Newhouse et al. ............. 128/203.15 |
| 5,437,271 | 8/1995 | Hodson et al. ............... 128/203.15 |

FOREIGN PATENT DOCUMENTS

| 2124519 | 11/1994 | Canada. |
| 0 078 685 | 5/1983 | European Pat. Off. |
| 0 198 708 | 10/1986 | European Pat. Off. |
| 0 565 489 | 10/1993 | European Pat. Off. |
| 2517209 | 6/1983 | France. |
| 2519254 | 7/1983 | France. |
| 578068 | 10/1977 | Russian Federation. |
| 610309 | 10/1948 | United Kingdom. |
| 643262 | 9/1950 | United Kingdom. |
| 1155988 | 6/1969 | United Kingdom. |
| 1308322 | 2/1973 | United Kingdom. |
| 1436576 | 5/1976 | United Kingdom. |
| 1487676 | 10/1977 | United Kingdom. |
| 2014047 | 8/1979 | United Kingdom. |
| 2104393 | 9/1983 | United Kingdom. |
| 2152197 | 7/1985 | United Kingdom. |
| WO84/01293 | 4/1984 | WIPO. |
| WO94/19044 | 9/1994 | WIPO. |

Primary Examiner—Kimberly L. Asher
Attorney, Agent, or Firm—Ross J. Oehler

[57] ABSTRACT

There is provided a device for the administration of an inhalation medicament, including a body defining a through-going air pathway having a longitudinal axis, an air inlet, an air outlet forming a mouthpiece, means for dispensing medicament into the pathway and air flow regulating means, characterised in that the air flow regulating means includes a movable obstructing means adapted to reduce the cross-sectional area of the pathway at a location between the air inlet and the means for dispensing medicament, and biassing means, whereby the obstructing means is biassed into a first resting position in which the cross-sectional area of the pathway is minimum and is adapted to move against the bias of the biassing means to a second position in which the cross-section area of the pathway is maximum in response to a pressure fall at the moiuthpiece caused by inhalation and is adapted to move further to a third position in which the cross-sectional area of the pathway is less than maximum in response to a greater pressure fall at the mouthpiece caused by inhalation.

25 Claims, 14 Drawing Sheets 5,727,546

POWDER INHALER WITH BREATH FLOW REGULATION VALVE

FIELD OF THE INVENTION

This invention relates to an inhalation device incorporating novel means for regulating the rate of patient inspiration.

BACKGROUND OF THE INVENTION

Known inhalation devices suitable for the administration to the lung of any inhalation medicament include devices which administer the medicament in liquid form, in dry powder form or as a suspension of the solid medicament in a liquified propellant.

Devices of the first mentioned type include nebuliser devices wherein a fine respirable mist is formed by action of a compressed gas on a sample, by vibration of a piezoelectric crystal or by other ultrasonic means; also, devices of the type described in e.g. International Patent Application WO 91/14468, where the liquid is sprayed through a small aperture.

Devices of the second mentioned type which may provide the medicament in unit dose or multidose form include the well known SPINHALER (Registered Trademark), which is described in UK Patent 1122284, the TURBUHALER (Registered Trademark) which is described in U.S. Pat. No. 4,524,769, and the device described in European Patent Application 407028.

Devices of the third mentioned type, which generally contain a pressurised reservoir of liquified propellant containing a suspension of the solid medicament and a metering valve for dispensing a suitable dose, are also very well known in the art and is not necessary to describe any particular type here.

However, it is a general problem with the above devices that the efficiency of administration of an accurate dose of medicament to the lung is severely impaired in the absence of any control of the flow of air through the device. In general, excessive inhalation velocity causes a significant proportion of the dose to impinge on the back of the throat, with a resultant short dose reaching the target area in the lungs. By contrast, a very low inhalation velocity results in poor dispersion of the medicament particles. This is known to be a particular problem of devices of the dry powder type which are gaining popularity due to their environmentally friendly attributes.

One way of alleviating the above problem in a dry powder device is described in U.S. Pat. No. 5,161,524 (Glaxo) wherein the inhalation device is provided with a secondary air conduit as well as the primary air conduit which provides the path for the inhalation medicament to the lung. If the air flow velocity becomes too great through the primary air conduit, then the secondary air conduit opens further thus decreasing the air velocity in the primary air conduit.

BRIEF SUMMARY OF THE INVENTION

However, this arrangement suffers from the disadvantage that whilst the velocity of air in the primary conduit may be reduced, a large volume of non drug-containing air is drawn in through the secondary air conduit, with the result that the breath of air necessary to secure a proper dose can become very long and drawn out. Furthermore, the arrangement may not be suitable for all the types of inhalation device described previously.

GB-A-2104393 (Glaxo) relates to an inhalation device comprising a housing for medicaments in an aerosol container. The device includes a valve located in a passage between the housing and an outlet. In use, the valve closes if the rate of flow of air inhaled by a patient exceeds a pre-determined amount.

There is provided a device for the administration of an inhalation medicament, including a body defining a through-going air pathway having a longitudinal axis, an air inlet, an air outlet forming a mouthpiece, means for dispensing medicament into the pathway and air flow regulating means, characterised in that the air flow regulating means includes a movable obstructing means adapted to reduce the cross-sectional area of the pathway at a location between the air inlet and the means for dispensing medicament, and biassing means, whereby the obstructing means is biassed into a first resting position in which the cross-sectional area of the pathway is minimum and is adapted to move against the bias of the biassing means to a second position in which the cross-section area of the pathway is maximum in response to a pressure fall at the mouthpiece caused by inhalation and is adapted to move further to a third position in which the cross-sectional area of the pathway is less than maximum in response to a greater pressure fall at the mouthpiece caused by inhalation.

DETAILED DESCRIPTION OF PREFERRED EMBODIMENTS

However, this arrangement has no influence on the minimum flow rate through the device.

We have now invented an inhalation device with breath rate control which overcomes or significantly mitigates these difficulties.

Thus, according to a first aspect of the invention we provide a device for the administration of an inhalation medicament as defined in claim 1.

By "obstructing means" we mean any element made of a material which is wholly or partially impervious to air and which is suitable for restricting the flow of air through the pathway. The obstructing means may be manufactured from a metal, plastic, rubber or other suitably dense material and may be of entirely solid contruction, or it may be made partially permeable to air by the provision of channels.

By "biassing means" we mean any means for providing a restraint to movement against the bias on the application of pressure or suction which also provides a restoring force in the opposite direction on the release of pressure or suction. Suitable biassing means include springs, where the spring may be compressed or stretched, for example, coil, torsion or leaf springs; elastomeric materials which are reversibly deformable; and resilient curved materials (including those made of metal, rubber or plastic) where the curve may be reversibly straightened.

The pressure fall at the mouthpiece may desirably be amplified by providing an air inlet which is constricted. Thus, we prefer that the cross-sectional area of the air inlet is less than the maximum cross-sectional area of the pathway. We particularly prefer that the air inlet comprises one or more apertures that have a total cross-sectional area of less than 25%, especially 10%, more especially 5% of the maximum cross-sectional area of the pathway.

Without prejudice to the generality of the concept, the following combinations of integers are preferred:

(a) the obstructing means comprises one or more partitions adapted to slide across the pathway along an axis perpendicular to the longitudinal axis of the pathway thereby obstructing the pathway. We prefer in this case that the biassing means comprises a spring; or (b) the obstructing means comprises an annular segment of membrane which connects two portions of the body. We particularly prefer that the obstructing means comprises a segment of membrane made of elastomeric material and the biassing means comprises the resistance of the elastomeric material to stretching in a direction perpendicular to the longitudinal axis of the pathway or that that the obstructing means comprises an annular segment of membrane made of inelastic material and the biassing means provides a bias against movement of the two portions of the body towards each other along the longitudinal axis of the pathway. In this latter case, we prefer that the biassing means comprises a spring; or (c) the obstructing means comprises a rigid grille or perforated sheet formed in a plane perpendicular to the longitudinal axis of the pathway on the air inlet side of which rests a flap which in its resting position is deflected towards the air inlet and in its second position is urged against the grille or perforated sheet. We particularly prefer that the flap is rigid and is hinged about an axis perpendicular to the longitudinal axis of the pathway and the biassing means comprises a spring at the hinge of the flap; or that the flap is made of a resilient elastomeric material and the biassing means consists of curvature introduced into the flap, said curvature being directed towards the air inlet; or (d) the obstructing and biassing means together comprise two or more cooperating flaps made of resilient elastomeric material which in the first position are deflected towards the air inlet and which in the second position are urged together thus reducing the cross-sectional area of the pathway.

The air flow regulating means described above are adapted to regulate the maximum and minimum velocity of airflow through the device.

We prefer that the second movable obstructing means is adapted to reduce the cross-sectional area of the pathway at a location between the first obstructing means and the means for dispensing medicament.

We prefer that the second biassing means comprises a spring biassed along the longitudinal axis of the device and the second obstructing means comprises a shutter mounted on the spring.

We prefer that the first obstructing means and biassing means comprise the elements described above as (a) to (d). We particularly prefer that the first obstructing means has the construction described in (c) above.

We prefer that the cross-sectional area of the pathway when the second obstructing means is in the first position is substantially zero.

As an alternative and preferred construction, which has the benefit of an economy of space, the first and second obstructing means may be combined into a single element which may move between 3 positions.

Thus, according to a second aspect of the invention, we provide a device for the administration of an inhalation medicament, including a body defining a through-going air pathway having a longitudinal axis, an air inlet, an air outlet forming a mouthpiece, means for dispensing medicament into the pathway and air flow regulating means, characterised in that the air flow regulating means includes a movable obstructing means adapted to reduce the cross-sectional area of the pathway at a location between the air inlet and the means for dispensing medicament, and biassing means, whereby the obstructing means is biassed into a first resting position in which the cross-sectional area of the pathway is minimum and is adapted to move against the bias of the biassing means to a second position in which the cross-sectional area of the pathway is maximum in response to a pressure fall at the mouthpiece caused by inhalation and is adapted to move further to a third position in which the cross-sectional area of the pathway is less than maximum in response to a greater pressure fall at the mouthpiece caused by inhalation.

The following combination of integers are preferred:

(A) the obstructing means is provided with an outer groove which is retained in the housing by means of a flange within the housing around which it fits loosely; or (B) the obstructing means is provided with an outer flange and which is retained in the housing by means of a groove within the housing within which it fits loosely; or (C) the obstructing means comprises a V-shaped vane, biassed at a hinge formed at the apex of the V, which rotates about an axis perpendicular to that of the pathway; or (D) the pathway is divided by a partition provided with a first aperture and the obstructing means comprises a shutter provided with a second aperture slidably engaged with the partition, which shutter is made to slide against the partition against the bias of the biassing means by a piston in gaseous communication with the mouthpiece.

In the case of (A) to (D) above, we prefer that the biassing means comprises a spring.

In the case of (C) above, we prefer that the biassing means comprises a spring at the hinge.

The following combination of integers is also preferred:

(E) the biassing means and obstructing means together comprise a perforated diaphragm made of resilient elastomeric material formed in a plane perpendicular to the longitudinal axis of the pathway. We particularly prefer that the diaphragm is provided with one or more protrusions on its upper and lower surfaces and is located between two partitions formed in a plane perpendicular to the longitudinal axis of the pathway, the partitions being provided with apertures with which some or all of said protrusions cooperate to restrict or prevent the passage of air through the apertures. We prefer the protrusion(s) to be of conical shape or to be of a shape consisting of a cone mounted on a cylinder. We prefer the aperture(s) with which the protrusion(s) cooperate to be circular. We prefer that the upper and lower surfaces of the diaphragm are each provided with a single protrusion.

In the case of (A), (B) and (E) above, we prefer that the obstructing means is of substantially circular section along an axis perpendicular to the longitudinal axis of the pathway. In the case of (C) and (D) above, we prefer that the obstructing means is of substantially square or rectangular section along an axis perpendicular to the longitudinal axis of the pathway.

We prefer that the cross-sectional area of the pathway when the obstructing means is in the first position, is substantially zero.

The device body defining the through going-pathway will be made of a rigid material, for example plastic or metal, and is preferably of substantially circular or square cross-section, although the shape of the section may at least in part be determined by the nature of the obstructing means.

The inhalation device according to the invention is particularly suitable for desired air flows in the range 20–250 l/min, especially 30–120 l/min, particularly 40–80 l/min. Pressure reduction that may be created between the air inlet and the mouthpiece in a device according to the invention, will typically be in the range 0.1–20 mbar.

It will be apparent that the air flow regulating means may be provided as an integral part of the housing of the inhalation device or as a separately manufactured portion of the device which may be affixed to the remainder of the inhalation device by means of a weld, a male-female type connection, a screw-thread or a mechanical equivalent. The affixation may be permanent, or it may provide for the two portions to be attached and detached as desired, for example, to facilitate cleaning of the device. We prefer that the air flow regulating means is adapted to be reversibly attached to and detached from the remainder of the device.

As a third aspect of the invention, we provide an air flow regulating means as described above adapted for use in conjunction with a device for the administration of an inhalation medicament.

Inhalation devices for use in accordance with the invention include any device conventionally used for dispensing powdered medicament for inhalation. Suitable devices include single dose dry powder inhalers e.g. the SPIN-HALER (Registered Trademark) inhaler and the DIS-KHALER (Registered Trademark) inhaler and multi-dose powder inhalers e.g. the TURBUHALER (Registered Trademark) inhaler and the device described in European Patent Application 407028.

We prefer that the device is a device for the inhalation of a dry powdered medicament or a medicament in aqueous solution. We particularly prefer that the device is a device for the inhalation of a dry powdered medicament.

Devices for inhalation of a medicament according to the invention are advantageous in that they are more effective or efficient, give a greater therapeutic benefit, are safer, are easier or cheaper to manufacture or assemble than those of the prior art. They are also advantageous in that, in use, the flow of air to the patient is more desirably or accurately controlled, the patient is able to obtain a larger or more consistent dose of medicament or they have other more desirable properties than known inhalation devices.

Preferred embodiments of the present invention will now be described, by way of example, with reference to the accompanying drawings in which the movement of air is shown by arrows.

FIG. 1 (a), shows a longitudinal section through an illustrative inhalation device similar to the SPINHALER (Registered Trademark) incorporating air flow regulating means, according to the second aspect of the invention, in the resting position.

In subsequent figures the details of the inhalation device are omitted for convenience.

Figure 1A:
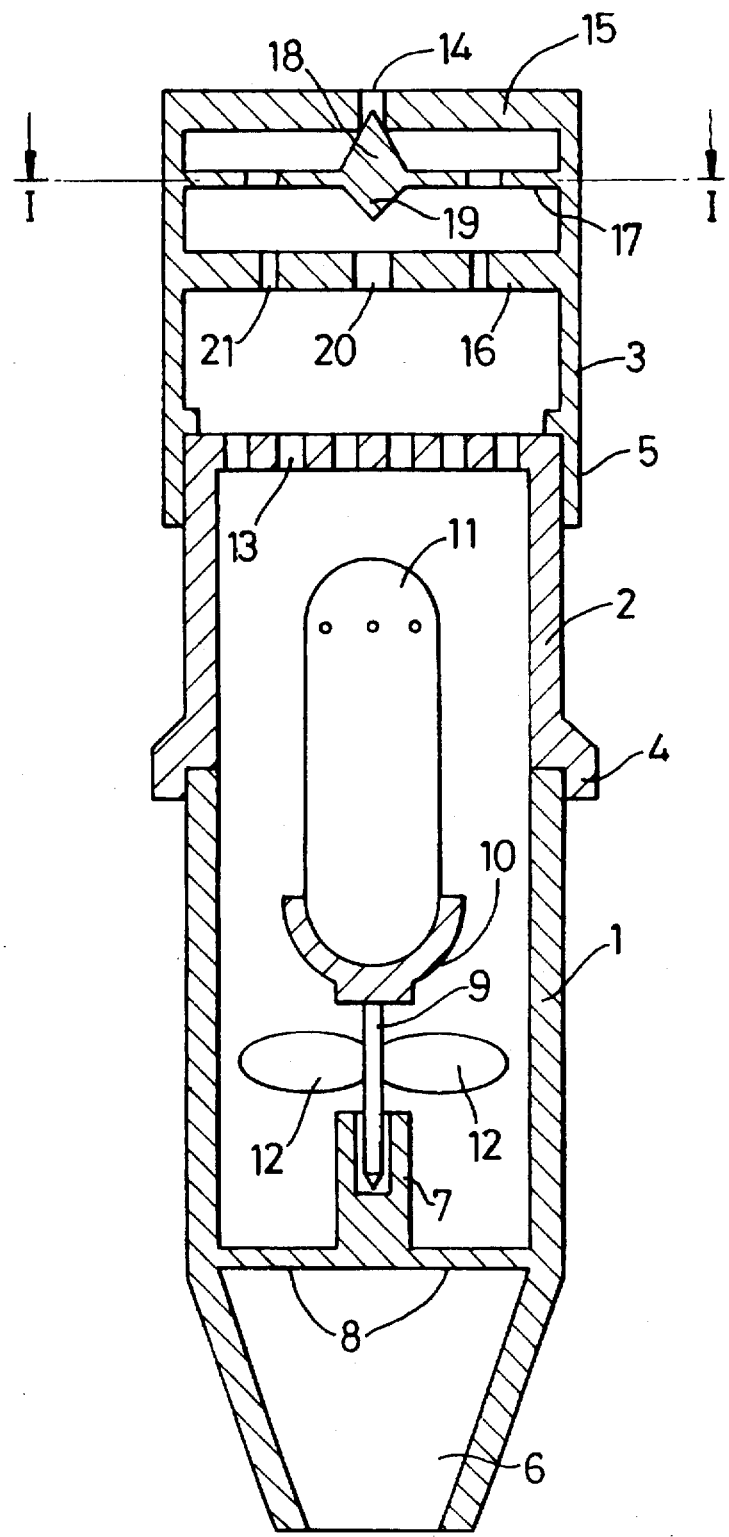
FIG. 1(b) shows a longitudinal section through the device of FIG. 1(a) with the air flow regulating means in the second position in which the cross-sectional area of the air pathway is maximum.
FIG. 1 (c) shows a longitudinal section through the device of FIG. 1(b) with the air flow regulating means in a third position in which the cross-sectional area of the pathway is less than maximum.
FIG. 1(d) shows a cross-section along line I—I of FIG. 1(a).

Referring now to FIG. 1(a) in more detail, a dry powder inhalation device comprises a generally cylindrical body defining a through-going pathway, said body comprising a mouth piece portion 1, a closure portion 2 and an air-flow regulator portion 3. Closure portion 2 is provided, at its end which connects with mouthpiece portion 1, with a peripheral flange 4 within which the end of mouthpiece portion 1 fits closely. Air flow regulator portion 3 is provided, at its end which connects with closure portion 2, with a peripheral flange 5 within which the end of closure portion 2 fits closely. At its end remote from air flow regulator portion 3, mouthpiece portion 1 is tapered to form a frustoconical mouthpiece 6. Within mouthpiece portion 1 a simple bearing 7 is supported by cross members 8. A spindle 9 is seated in bearing 7. Spindle 9 is provided with a cup 10 which is capable of closely receiving a perforated capsule 11 containing medicament to be inhaled, which together form means for dispensing medicament. Spindle 9 is also provided with rotor vanes 12 which cause spindle 9 to rotate within bearing 7 when air is drawn through the device, as during inhalation. Closure portion 2 is provided, at its end remote from the mouthpiece portion 1, with a perforated grid 13.

Air flow regulator portion 3, having an air inlet aperture 14 in first partition 15 is provided with a second partition 16 on the mouthpiece side of the first partition 15 in between which two partitions is located a perforated diaphragm 17. Perforated diaphragm 17 is provided with a protrusion 18 on the inlet side which cooperates with and closes air inlet aperture 14 in first partition 15 in the resting position and a protrusion 19 on the outlet side which is adapted to cooperate with and close an aperture 20 in second partition 16 in response to a pressure drop at the mouthpiece caused by inhalation. Second partition 16 also contains further apertures 21.

Figure 1B:
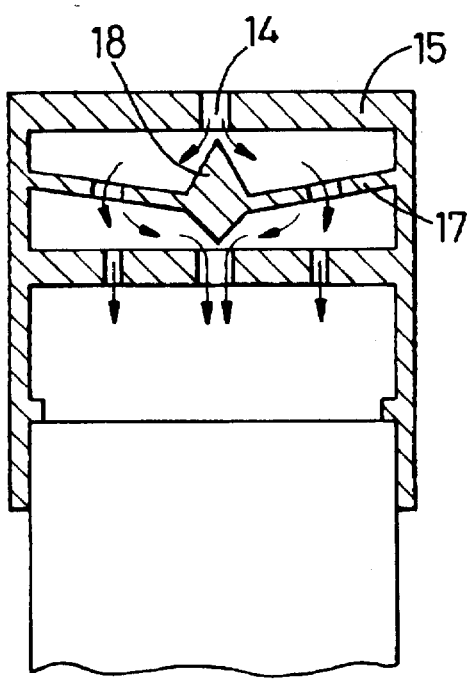

Referring now to FIG. 1(b), in use, when the pressure at the mouthpiece (not shown) is reduced on inhalation, the perforated diaphragm 17 is distorted and protrusion 18 moves away from air inlet aperture 14 in first partition 15 thus allowing the flow of air through the pathway via perforations in the diaphragm 17.

Figure 1C:
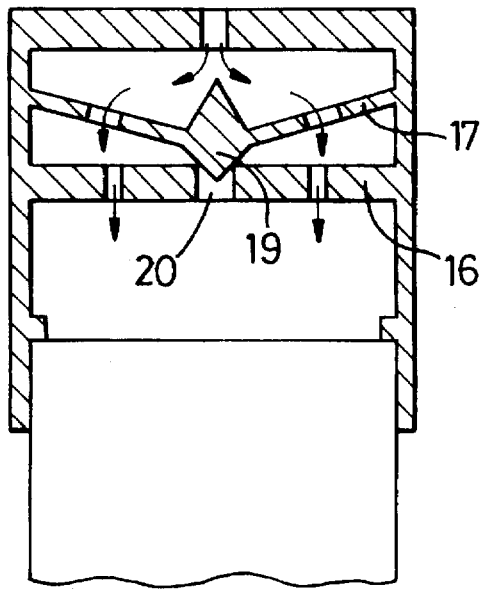

Referring now to FIG. 1(c), when the pressure at the mouthpiece is further reduced, protrusion 19 on the air outlet side of perforated diaphragm 17 is urged against aperture 20 in second partition 16 thus reducing the cross-sectional area of the pathway and restricting the flow of air.

Figure 1D:
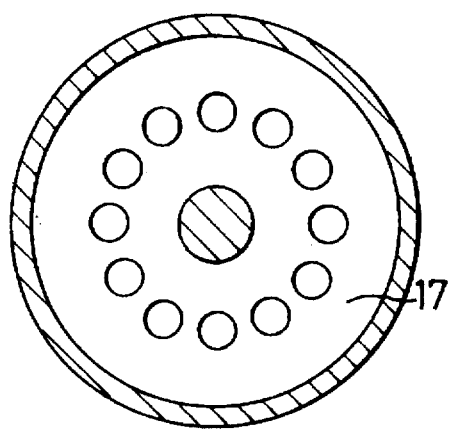

FIG. 1(d) shows a possible arrangement of perforations in diaphragm 17.

As variants of the embodiment shown in FIG. 1, perforated diaphragm 17 may be provided with any number of protrusions 18 to its surface on the air inlet side which cooperate with an equal number of apertures 14 in first partition 15. In an alternative arrangement, there may exist an excess number of apertures 14 over the number of protrusions 18. Equally, perforated diaphragm 17 may be provided with one or more protrusions 19 to its surface on the outlet side which cooperate with an equal number of apertures 20 in second partition 16, or the number of apertures 20 in partition 16 may exceed the number of protrusions 19 on perforated diaphragm 17.

In FIGS. 2 to 12 which follow, the details of construction of portions 1 and 2 of the inhalation device are omitted but may readily be ascertained by reference to FIG. 1(a).

Figure 2A:
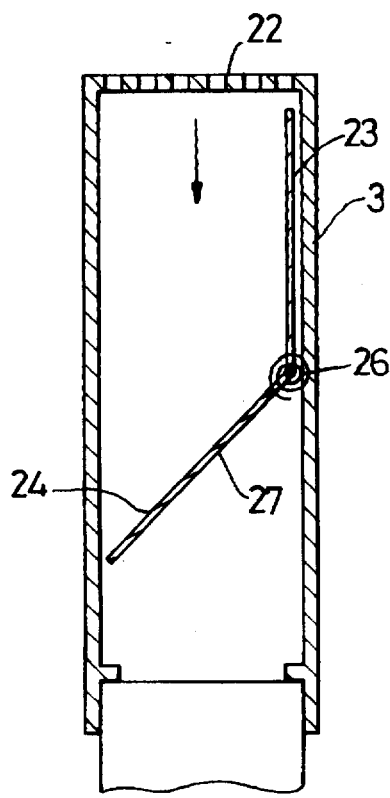
FIG. 2(a) shows a longitudinal section through a device according to the second aspect of the invention showing the air flow regulating means in the resting position.
Figure 2B:
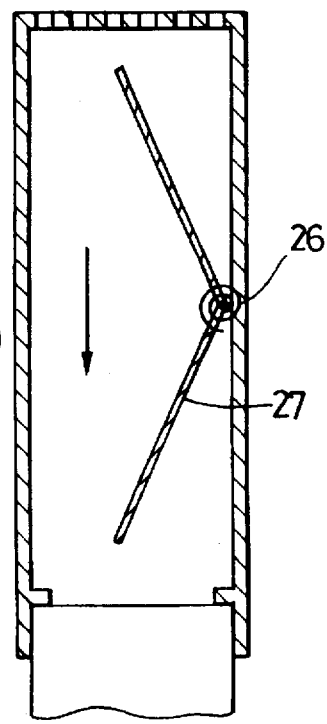
FIG. 2(b) shows a longitudinal section through the device of FIG. 2(a) with the air flow regulating means in a second position in which the cross-sectional area of the air pathway is maximum.
Figure 2C:
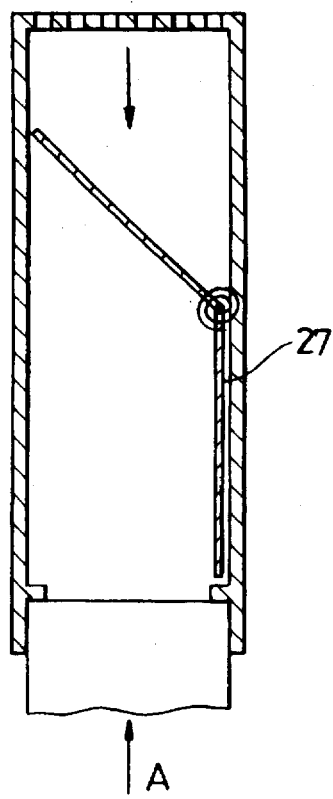
FIG. 2(c) shows a longitudinal section through the device of FIG. 2(a) with the air flow regulating means in a third position in which the cross-sectional area of the pathway is less than maximum.
Figure 2D:
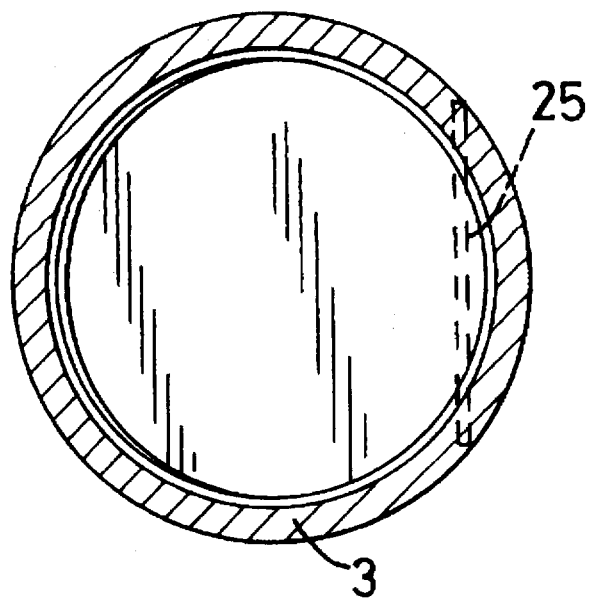
FIG. 2(d) shows a plan view of the device of FIG. 2(c) with the airflow regulating means in the third position taken from the direction of arrow A and in which the cross-section is circular.
Figure 2E:
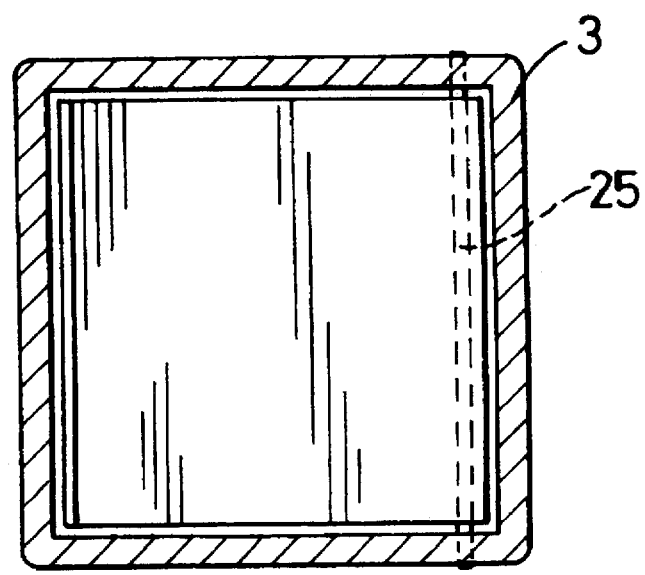
FIG. 2(e) is similar to FIG. 2(d) save that the cross-section is square.

Referring now to FIG. 2(a) the air flow regulator portion 3 of the inhalation device, comprises an air inlet 22 and contains a hinged V-shaped vane 27 having two portions 23 and 24 which is able to rotate about an axis perpendicular to the pathway at a hinge 25 (shown in FIGS. 2(d) and 2(e)) against the bias of spring 26. In the resting position, the cross-sectional area of the pathway is substantially zero.

Referring now to FIG. 2(b), when the pressure at the mouthpiece (not shown) is reduced on inhalation, vane 27 rotates about its axis against the bias of spring 26, thus increasing the cross-sectional area of the pathway and allowing the flow of air. At a point at which the vane has half rotated, the flow of air is maximum.

Referring now to FIG. 2(c), when the pressure at the mouthpiece is further reduced, the vane 27 further rotates until it is unable to rotate any further at which point the flow of air is again minimised.

The two portions 23, 24 of vane 27 may be gas impermeable, in which case the flow of air at rest and at minimum pressure at the mouthpiece will be entirely prevented, or either or both portions may be perforated, in which case some flow of air will be allowed when the flow regulator portion 3 of the inhalation device is in the first or third positions.

Figure 3A:
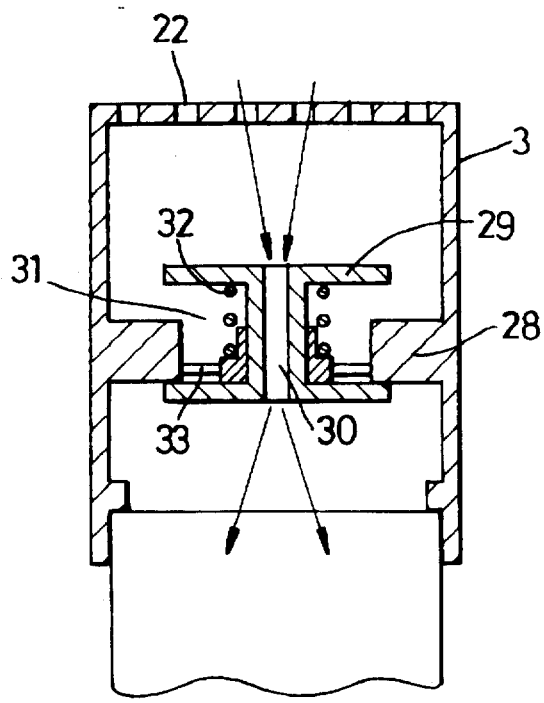
FIG. 3(a) shows a longitudinal section through a device according to the second aspect of the invention with the air flow regulating means in the resting position.

Referring now to FIG. 3(a), air flow regulator portion 3 of the inhalation device comprises an air inlet 22 and is provided with an annular flange 28 which retains a disc 29 having a central channel 30 and an outer groove 31 in which the flange 28 fits loosely. The groove 31 in disc 29 is biased against the air outlet side of flange 28 by means of spring 32 which is supported by a protrusion 33 on flange 28.

Figure 3B:
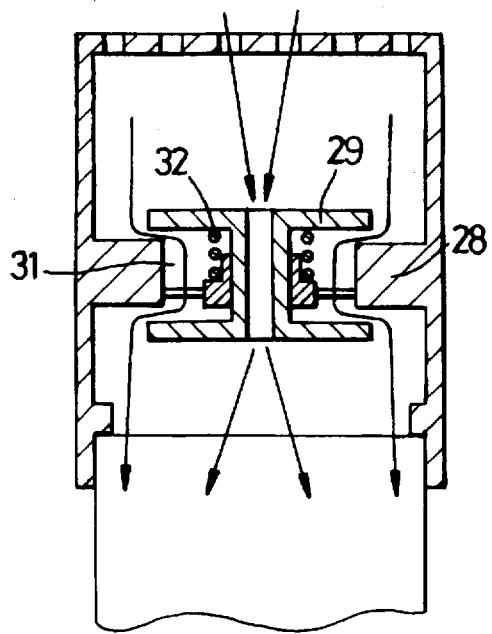
FIG. 3(b) shows a longitudinal section through the device of FIG. 3(a) with the air flow regulating means in a second position in which the cross-sectional area of the air pathway is maximum.

Referring now to FIG. 3(b), when the pressure at the mouthpiece (not shown) is reduced on inhalation, the disc 29 moves against the bias of spring 32 thus creating a space between the flange 28 and the groove 31 on the disc 29 through which air may flow.

Figure 3C:
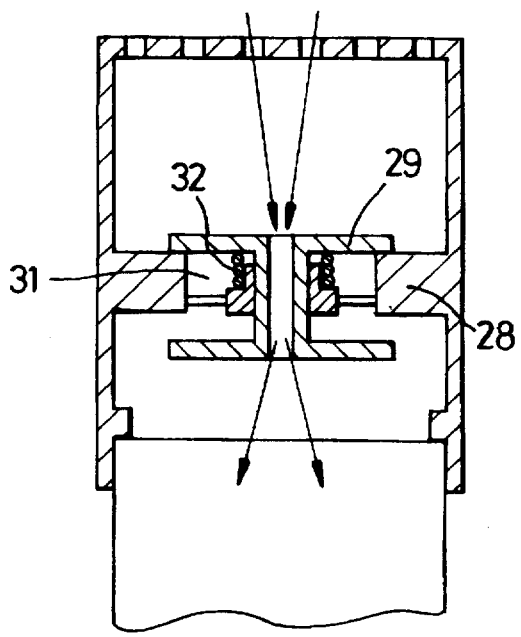
FIG. 3(c) shows a longitudinal section through the device of FIG. 3(a) with the air flow regulating means in a third position in which the cross-sectional area of the pathway is less than maximum.

Referring now to FIG. 3(c), when the pressure at the mouthpiece is further reduced, the disc 29 moves further against the bias of spring 32 and the space formed between the flange 28 and the groove 31 on the disc 29 is closed. Thus the cross-sectional area of the pathway is decreased to that value in the resting position (FIG. 3(a)).

Figure 4A:
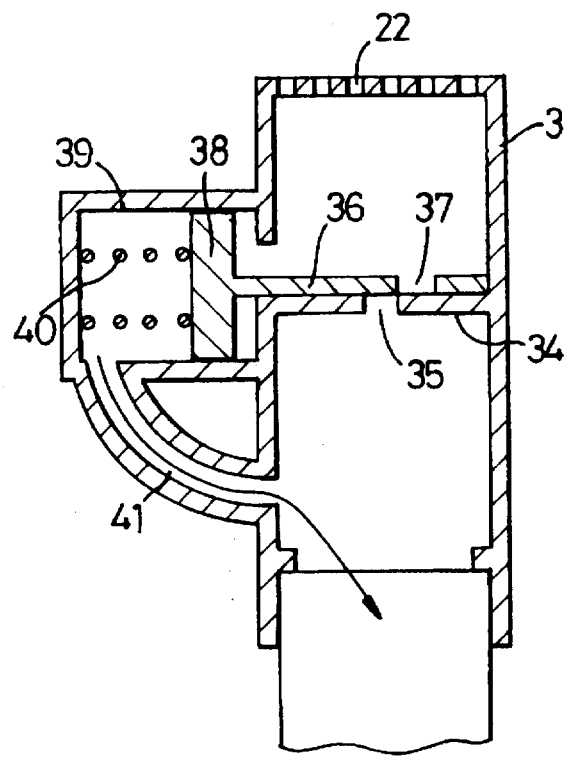
FIG. 4(a) shows a longitudinal section through a device according to the second aspect of the invention with the air flow regulating means in the resting position.

Referring now to FIG. 4(a), air flow regulator portion 3 of the inhalation device comprises an air inlet 22 and contains a partition 34 provided with a first aperture 35. Aperture 35 is, in the resting position, closed by a shutter 36 provided with a second aperture 37, which shutter is slidably engaged with the partition. Movement of the shutter 37 is controlled by a piston 38 retained in piston housing 39 which forms part of the housing of flow regulator portion 3 and which is biased against one or more springs 40. The piston 38 is in gaseous communication with the air outlet at the mouthpiece (not shown) by means of a channel 41 connecting the piston housing 39 and a part of the air flow regulator portion 3 on the air outlet side of the shutter 36.

Figure 4B:
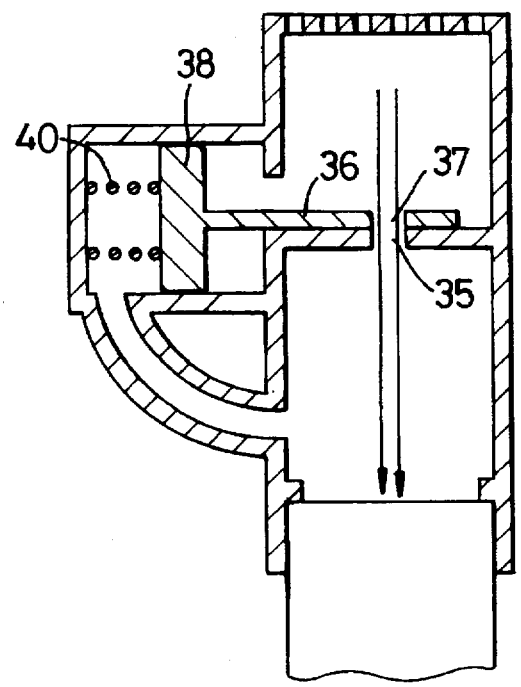
FIG. 4(b) shows a longitudinal section through the device of FIG. 4(a) with the air flow regulating means in a second position in which the cross-sectional area of the air pathway is maximum.

Referring now to FIG. 4(b), when the pressure at the mouthpiece (not shown) is reduced on inhalation, the piston 38 is urged against the bias of spring(s) 40, and the shutter 36 moves bringing second aperture 37 into communication with first aperture 35.

Figure 4C:
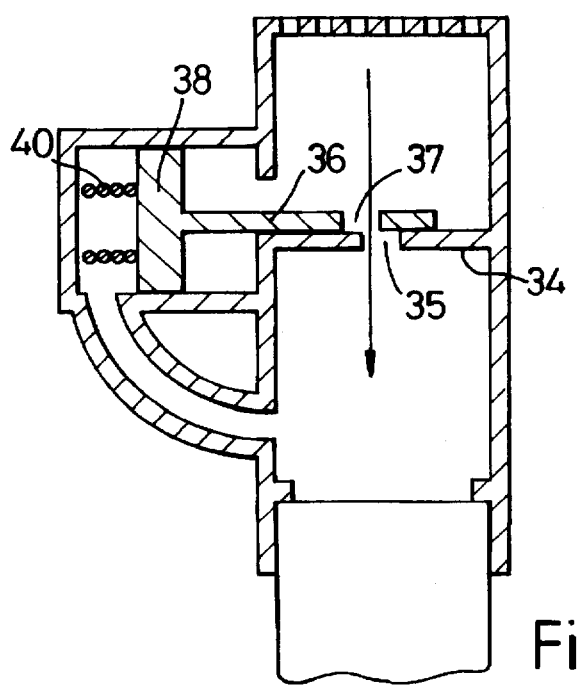
FIG. 4(c) shows a longitudinal section through the device of FIG. 4(a) with the air flow regulating means in a third position in which the cross-sectional area of the pathway is less than maximum.

Referring now to FIG. 4(c), as the pressure at the mouthpiece is further reduced, the piston 38 is urged further against the bias of spring(s) 40 and the aperture 37 in shutter 36 moves out of communication with the aperture 35 in partition 34, thus restricting the flow of air.

The relative dimensions of apertures 35 and 37 and the distance of travel of piston 38 may be such that the pathway is completely closed at rest when a pressure drop is produced at the mouthpiece, or that the cross-sectional area of the pathway under these conditions is small.

Figure 5A:
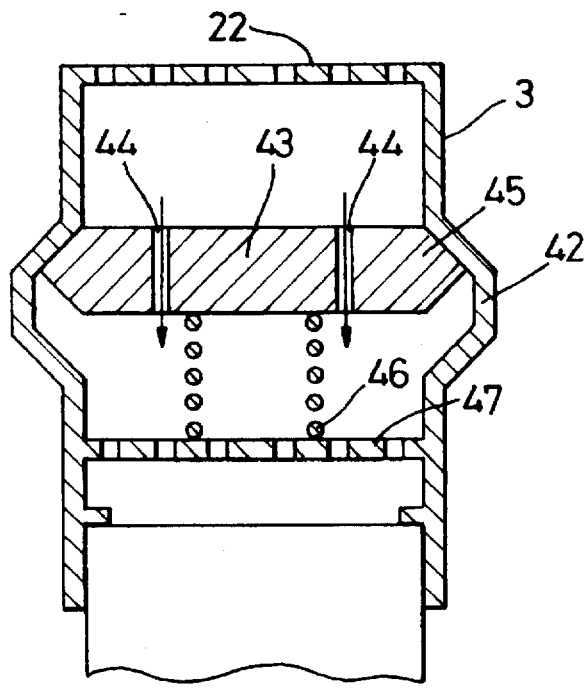
FIG. 5(a) shows a longitudinal section through a device according to the second aspect of the invention with the air flow regulating means in the resting position.

Referring now to FIG. 5(a), air flow regulator portion 3 of the inhalation device comprises an air inlet 22 and is provided with a circumferential groove 42 which retains a disc 43 having a central channel 44 and an outer flange 45 around which the groove 42 fits loosely. The flange 45 on disc 43 is biased against the inlet side of groove 42 in the housing by means of spring 46 which is supported by a base 47. Base 47 is illustrated as a grille; however it may alternatively consititute a protrusion into the pathway from the wall of the air flow regulator portion 3 at a point on the outlet side of the groove 42, or a cross-piece, or it may constitute some other mechanical equivalent which will be apparent to a person skilled in the art.

Figure 5B:
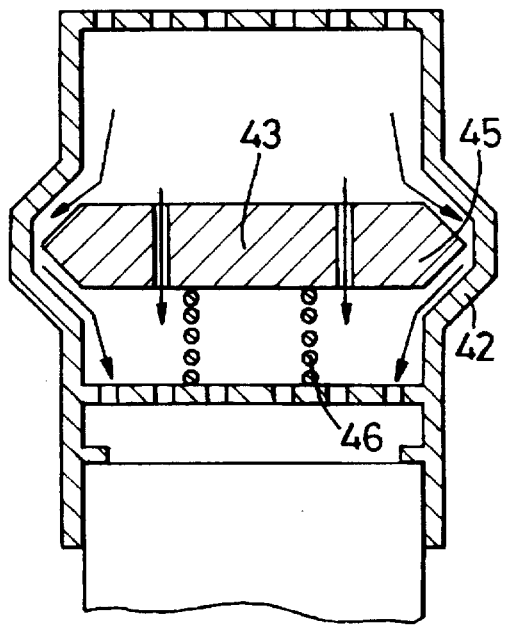
FIG. 5(b) shows a longitudinal section through the device of FIG. 5(a) with the air flow regulating in a second position in which the cross-sectional area of the air pathway is maximum.

Referring now to FIG. 5(b), when the pressure at the mouthpiece (not shown) is reduced on inhalation, the disc 43 moves against the bias of spring 46 thus creating a space between the flange 45 on the disc 43 and the groove 42 through which air may flow.

Figure 5C:
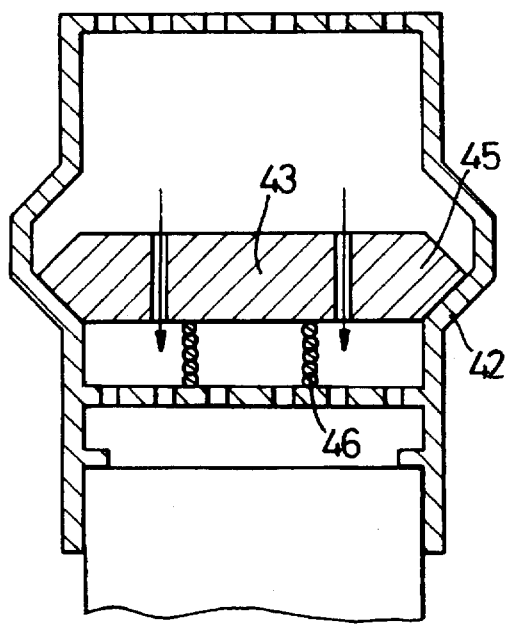
FIG. 5(c) shows a longitudinal section through the device of FIG. 5(a) with the air flow regulating means in a third position in which the cross-sectional area of the pathway is less than maximum.

Referring now to FIG. 5(c), when the pressure at the mouthpiece is further reduced, the disc 43 moves further against the bias of spring 46 and the space formed between the flange 45 on the disc 43 and the groove 42 is closed. Thus the cross-sectional area of the pathway is decreased to that value in the resting position (FIG. 5(a)).

In FIGS. 3 and 5, we prefer that the air flow regulator portion 3 and disc 29 or 45 are of circular section. However, they may also be of another shaped section, for example, of rectangular or square section.

Furthermore, it will be apparent to the skilled person that disc 29 or 45 may have any number of channels which may be arranged as desired. Alternatively, although this is not preferred, they may be entirely solid in which case the minimum flow rate will be zero.

Figure 6A:
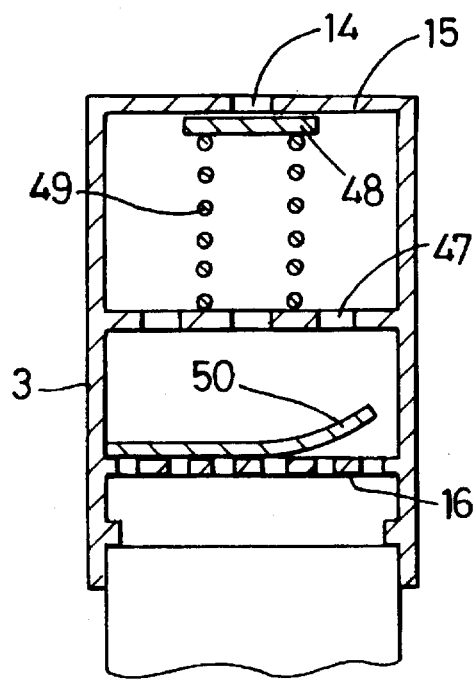
FIG. 6(a) shows a longitudinal section through a device according to the first aspect of the invention with an air flow regulating means having first and second obstructing means in the resting position.

Referring now to FIG. 6(a), air flow regulator portion 3 of the inhalation device, having an air inlet aperture 14 in first partition 15 is provided with a second perforated partition 16 towards the outlet, in between which is located a shutter 48 which is urged against air inlet aperture 14 by the bias of spring 49 and a curved resilient flap 50 made of elastomeric material which rests against second partition 16 on the air inlet side of second partition 16 and in which the curvature of the flap 50 is directed towards the air inlet.

Figure 6B:
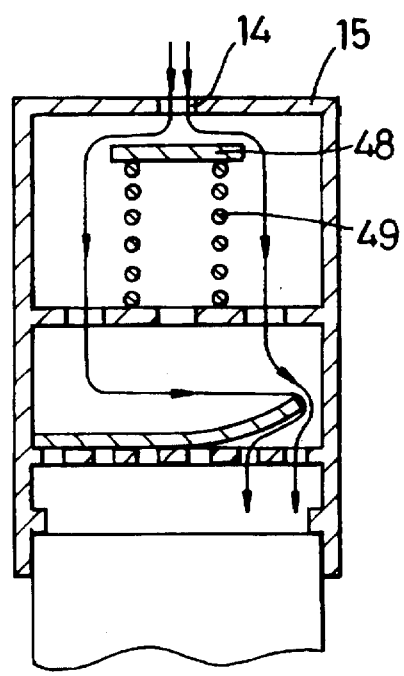
FIG. 6(b) shows a longitudinal section through the device of FIG. 6(a) wherein the second obstructing means is in a second position in which the cross-sectional area of the air pathway is more than minimum.

Referring now to FIG. 6(b), in use, when the pressure at the mouthpiece (not shown) is reduced on inhalation, the shutter 48 moves away from the air inlet aperture 14 in first partition 15 against the bias of spring 49 thus allowing air to be drawn through the device.

Figure 6C:
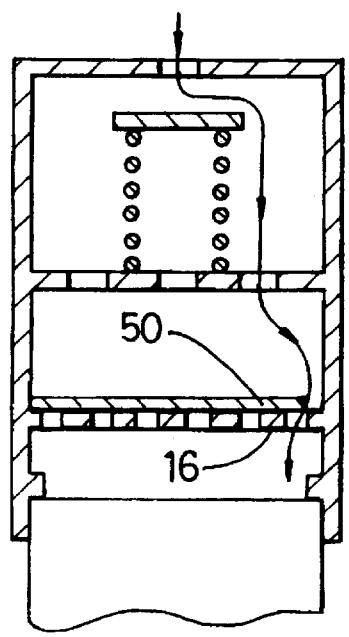
FIG. 6(c) shows a longitudinal section through the device of FIG. 6(b) wherein the first obstructing means is in a second position in which the cross-sectional area of the pathway is less than maximum.

Referring now to FIG. 6(c), when the pressure at the mouthpiece is further reduced, the flap 50 is urged against partition 16 with lessening of its curvature thereby reducing the cross-sectional area of the pathway and restricting the flow of air. Should the suction applied at the mouthpiece be reduced, the curvature of the flap is restored and the cross sectional area through which the air may pass is increased. In this way the flow of air through the device is regulated.

Figure 7A:
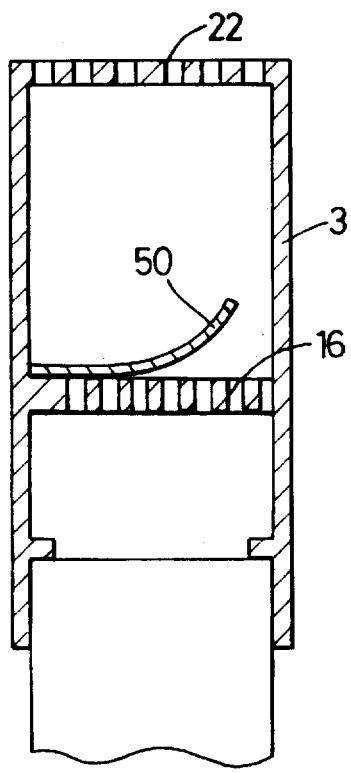
FIG. 7(a) shows a longitudinal section through a device outside the scope of the invention with the air flow regulating means in the resting position.
Figure 7B:
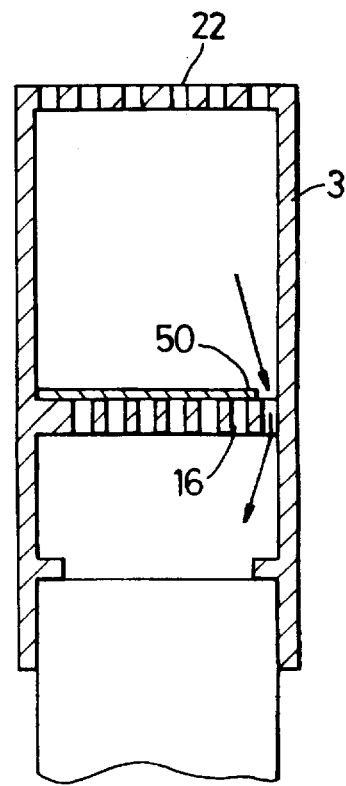
FIG. 7(b) shows a longitudinal section through the device of FIG. 7(a) with the air flow regulating means in a second position in which the cross-sectional area of the pathway is minimum.

Referring now to FIGS. 7(a) and 7(b), air flow regulator portion 3 of the inhalation device having an air inlet 22 is provided with a grille or perforated partition 16 on the air inlet side of which rests a curved resilient flap 50 made of elastomeric material, the curvature of which flap is directed towards the air inlet. The operation of the device in response to a varying strength suction applied at the mouthpiece is essentially as described above for FIGS. 6(b) and 6(c).

Figure 8:
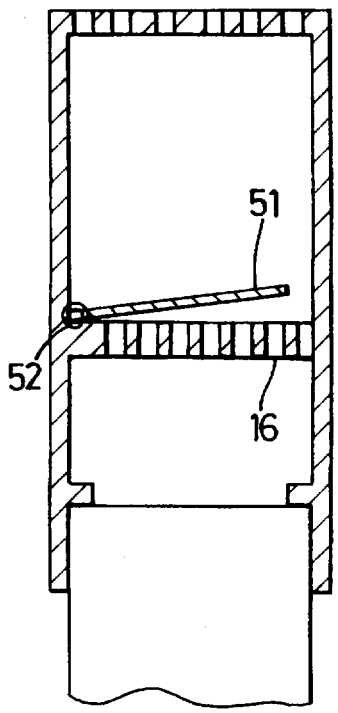
FIG. 8 shows a longitudinal section through a device outside the scope of the invention with the air flow regulating means in the resting position.

In FIG. 8, the curved resilient flap 50 of FIG. 7 is replaced by a rotatable rigid flap 51 which is hinged at the wall of the housing of the air flow regulator portion 3 such that the axis of rotation is perpendicular to the direction of air flow. At rest, the rigid flap 51 is biassed towards the air inlet by spring 52 located at the hinge. As the pressure at the mouthpiece (not shown) is reduced, rigid flap 51 is urged against perforated partition 16 thereby reducing the cross-sectional area of the air pathway and restricting the flow of air.

Figure 9A:
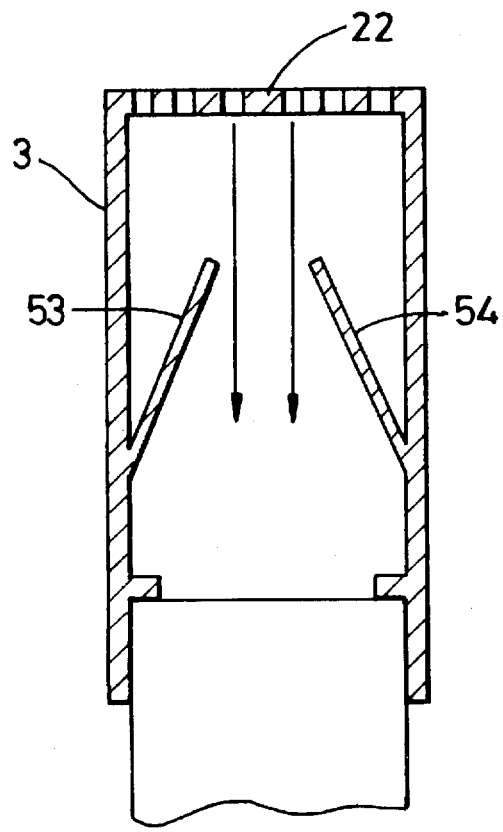
FIG. 9(a) shows a longitudinal section through a device outside the scope of the invention with the air flow regulating means in the resting position.

In FIG. 9(a), the housing of the air flow regulator portion 3 of the inhalation device, which we prefer to be of square section, and which is provided with an air inlet 22, contains two cooperating flaps 53, 54 of resilient elastomeric material which are deflected towards the air inlet.

Figure 9B:
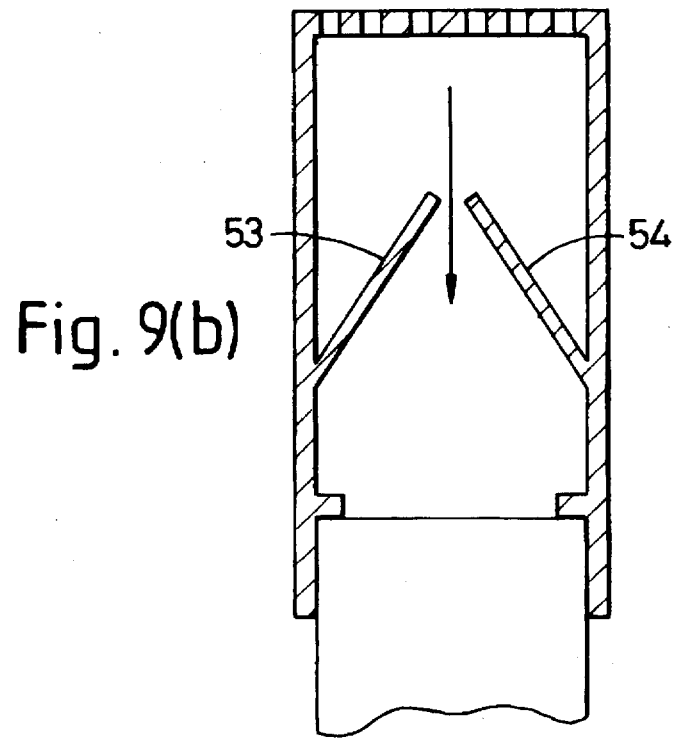
FIG. 9(b) shows a longitudinal section through the device of FIG. 9(a) with the air flow regulating means between the first and second positions.

Referring to FIG. 9(b), when the pressure at the mouthpiece (not shown) is reduced on inhalation, the flow of air through the pathway causes flaps 53 and 54 to be urged together, thus causing a reduction in the cross-sectional area of the pathway. The flow of air through the outlet is thus regulated in a similar manner to the embodiments shown in FIGS. 7 and 8.

Furthermore, a device similar to the embodiment shown in FIG. 9 may be imagined in which flaps 53, 54 are replaced by a larger number of flaps in a frusto-conical arrangement in which case the cross-section of the air flow regulator portion 3 is desirably circular.

Figure 10A:
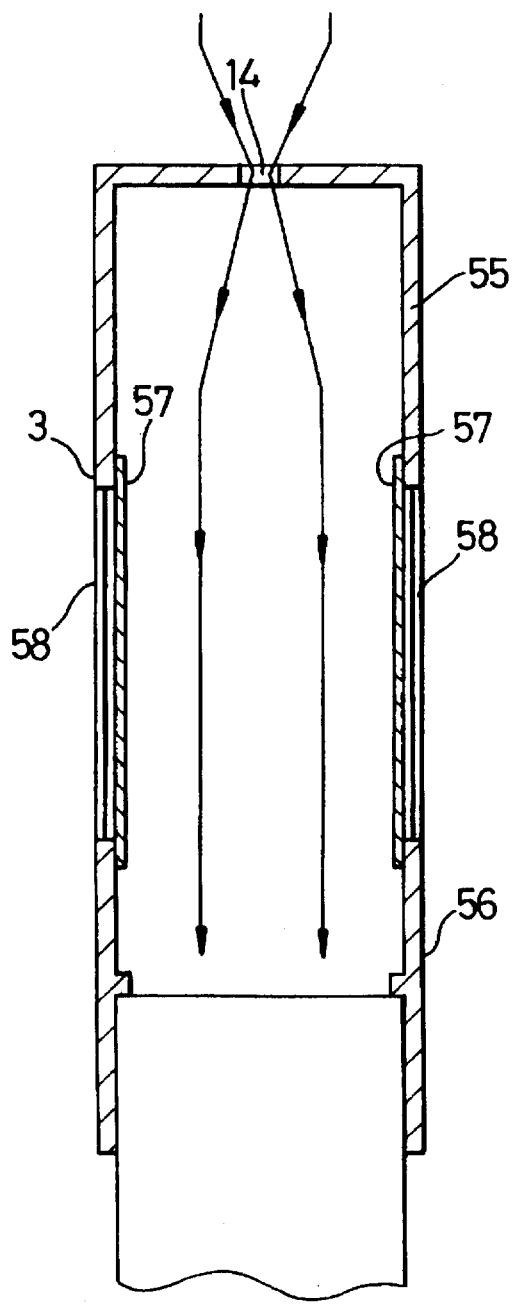
FIG. 10(a) shows a longitudinal section through a device outside the scope of the invention with the air flow regulating means in the resting position.

Referring now to FIG. 10(a), air flow regulator portion 3 of the inhalation device, consists of two portions 55 and 56, the former of which is provided with a constricted air inlet 14, the two portions of the housing being connected by an annular segment of membrane made of thin elastomeric material 57 held rigid by the presence of two or more solid supports 58.

Figure 10B:
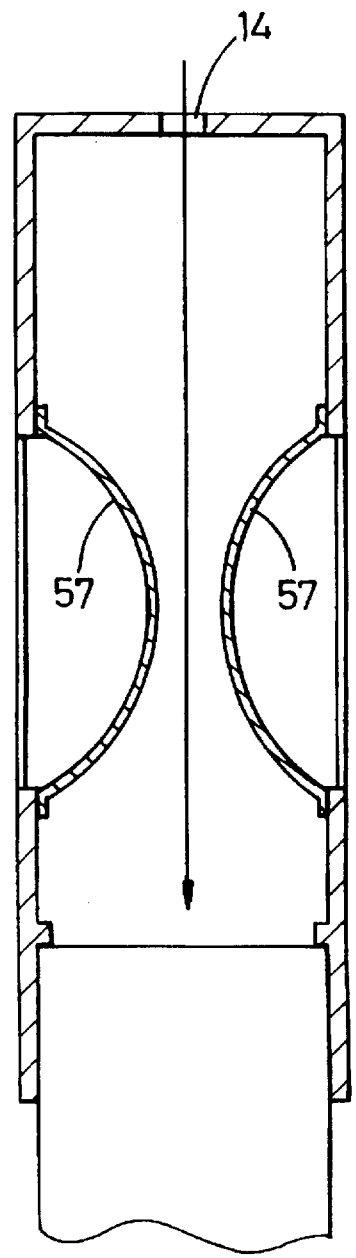
FIG. 10(b) shows a longitudinal section through the device of FIG. 10(a) with the air flow regulating means between the first and second positions.

Referring now to FIG. 10(b), as the pressure at the mouthpiece (not shown) is reduced on inhalation, a pressure difference (amplified by the constriction at air inlet 14) is created across the membrane 57 causing it to stretch against its bias into the air pathway. The air pathway is obstructed and its cross-sectional area is in this way reduced. As the pressure drop at the mouthpiece is reduced, the membrane 57 relaxes towards its rest position and the cross-sectional area of the pathway through which the air may pass is increased towards its maximum value. The stretching and relaxing of the membrane 57 is sensitive to the suction applied at the mouthpiece, and thus the flow of air through the device is regulated.

As a variant of the embodiment shown in FIG. 10 we envisage a further embodiment in which the elastomeric membrane is present not as an annular segment, but as two part semi-annular segments located diametrically opposite each other and in which the supports 58 are formed as an integral part of the housing tube. This variant on the tenth embodiment can be expected to operate in the same manner as the tenth embodiment, although it may have further advantages for example in ease of manufacture.

Figure 11A:
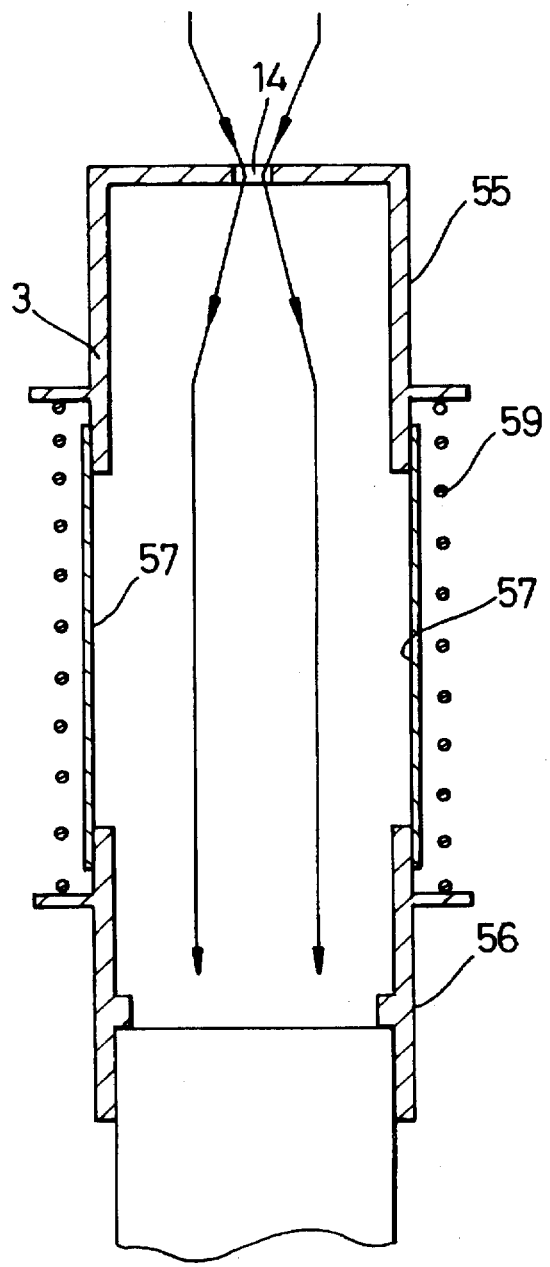
FIG. 11(a) shows a longitudinal section through a device outside the scope of the invention with the air flow regulating means in the resting position.

Referring now to FIG. 11(a), air flow regulator portion 3 of the inhalation device is of circular section and consists of two portions 55 and 56, the former of which is provided with a constricted air inlet 14, the two portions of the housing being connected by an annular segment of membrane made of inelastic material 57 held rigid and extended by the presence of spring 59.

Figure 11B:
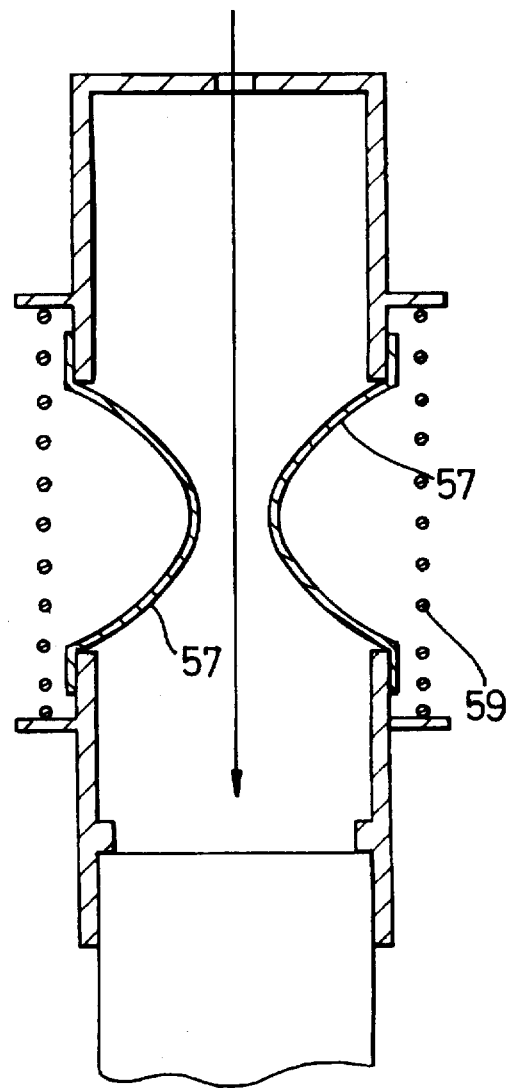
FIG. 11(b) shows a longitudinal section through the device of FIG. 11(a) with the air flow regulating means between the first and second positions.

Referring now to FIG. 11(b), as the pressure at the mouthpiece (not shown) is reduced on inhalation, a pressure difference is created across the membrane 57 causing it to crumple into the pathway. As the membrane 57 is inelastic, the two portions of the housing are drawn together against the bias of spring 59. The pathway is obstructed and its cross-sectional area is in this way reduced. As the pressure drop at the outlet is reduced, the spring 59 relaxes and the membrane 57 returns towards its rest position. The cross-sectional area of the pathway through which air may pass is thus increased towards its maximum value. In this way, and in a similar manner to the tenth embodiment, the flow of gas through the outlet is regulated.

As a variant of the embodiment shown in FIG. 11, we envisage a further embodiment in which the two portions of the air flow regulator portion 3 have square section separated by a segment of membrane made of inelastic material wherein this segment contains creases so that it is capable of compressing concertina fashion with simultaneous reduction in its cross-sectional area in the manner of an old-fashioned camera bellows.

Figure 12A:
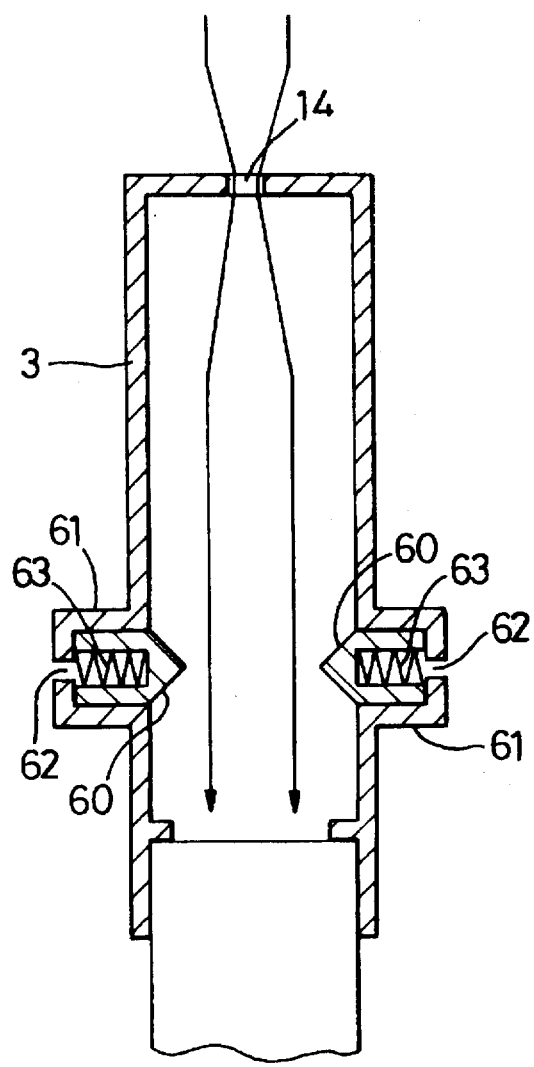
FIG. 12(a) shows a longitudinal section through a device outside the scope of the invention with the air flow regulating means in the resting position.

Referring now to FIG. 12(a), air flow regulator portion 3 of the inhalation device, having constricted air inlet 14 contains along its length two partitions 60 retained in pockets 61 in the housing of the air flow regulator portion 3, with which they form an airtight seal. Partitions 60 are adapted to slide along an axis perpendicular to the longitudinal axis of the device, and are in gaseous communication with the outside of the housing through airholes 62. Springs 63 bias partitions 60 into their resting position within pockets 61.

Figure 12B:
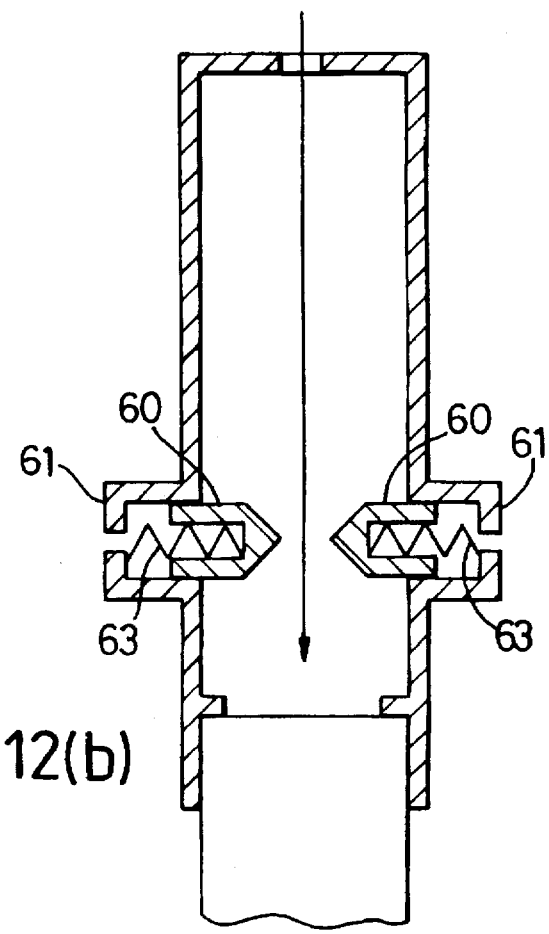
FIG. 12(b) shows a longitudinal section through the device of FIG. 12(a) with the air flow regulating means between the first and second positions.

Referring now to FIG. 12(b), as the pressure at the mouthpiece (not shown) is reduced on inhalation, a pressure difference is created between the inside and outside faces of the partitions 60 causing them to slide in a direction perpendicular to the longitudinal axis of the device against the bias of springs 63. The pathway is obstructed and its cross-sectional area is reduced. As the pressure reduction at the outlet is reduced, the springs 63 relax and the partitions 60 return to their rest positions within pockets 61. The cross-sectional area of the pathway through which the air may pass is thus increased towards its maximum value. In this way, the flow of air through the device is regulated.

Although it is not preferred, it can be seen that a variant on the twelfth embodiment may be provided which comprises only a single partition 60, but which will nevertheless operate in a similar manner.

It may be envisaged in the embodiments shown in FIGS. 1, 5, 6, 7 and 8 in order to improve compactness of the device that perforated grid 13 may be omitted from the construction, particularly if the closure portion 2 and the air flow regulator portion 3 are moulded as one piece rather than two.

Embodiments were tested experimentally to investigate their air flow characteristicsas follows:

Experimental Test 1

An inhalation device according to the invention was constructed which comprised a conventional SPINHALER (Registered Trademark) and an air flow regulator portion as illustrated in FIG. 6 in which the size of aperture 14 was 6.3 mm, the inside diameter of the housing of the air flow regulator portion was 20.7 mm, the elastomeric flap 50 was circular and manufactured of vulcanised rubber and the spring 49 consisted of a single turn of fine steel wire.

The device was tested using a vacuum generator to simulate patient inhalation. A maximum flow-rate was obtained at 41 l/min, which flow rate is known to be in the desirable range for efficient inhalation of dry-powdered medicament.

Experimental Test 2

An air flow regulator portion for an inhalation device according to the invention was constructed as illustrated in FIG. 1 in which the inside diameter of the air flow regulating portion 3 was 50 mm, the diameter of the aperture 14 was 5 mm, diaphragm 17 was constructed of silicone rubber of thickness 0.95 mm and protrusions 18 and 19 were manufactured of a rigid plastics material (acetal). Protrusions 18 and 19 were affixed to the diaphragm by means of a screw fixture on protrusion 18 which passed through the diaphragm 17 into a threaded socket within protrusion 19. An airtight cooperation between protrusion 18 and aperture 14 in the resting position was ensured by the provision of a 3 mm thick foam rubber surround to aperture 14. Diaphragm 17 contained a single circular perforation of diameter 5 mm. Three tests were performed with other dimensions as follows:

Test 2(a)

Diameter of the aperture 20: 6 mm;

Protrusion 18 consisted of a cone of height 10 mm and conical angle 40° sitting on cylindrical base of height 3 mm;

Protrusion 19 consisted of a cone of height 4 mm and conical angle 45° sitting on a cylindrical base of height 3 mm;

Distance between partition 15 and diaphragm 17: 3 mm;

Distance between partition 16 and diaphragm 17: 13 mm.

Test 2(b)

Dimensions as with Test 2(a) except for the following:

Distance between partition 15 and diaphragm 17: 2 mm:

Distance between partition 16 and diaphragm 17: 11 mm.

Partition 15 was provided with a second aperture of diameter 5 mm.

Test 2(c)

Dimensions as with Test 2(b) except for the following:

Distance between partition 15 and diaphragm 17: 3 mm;

Distance between partition 16 and diaphragm 17: 13 mm.

Figure 13:
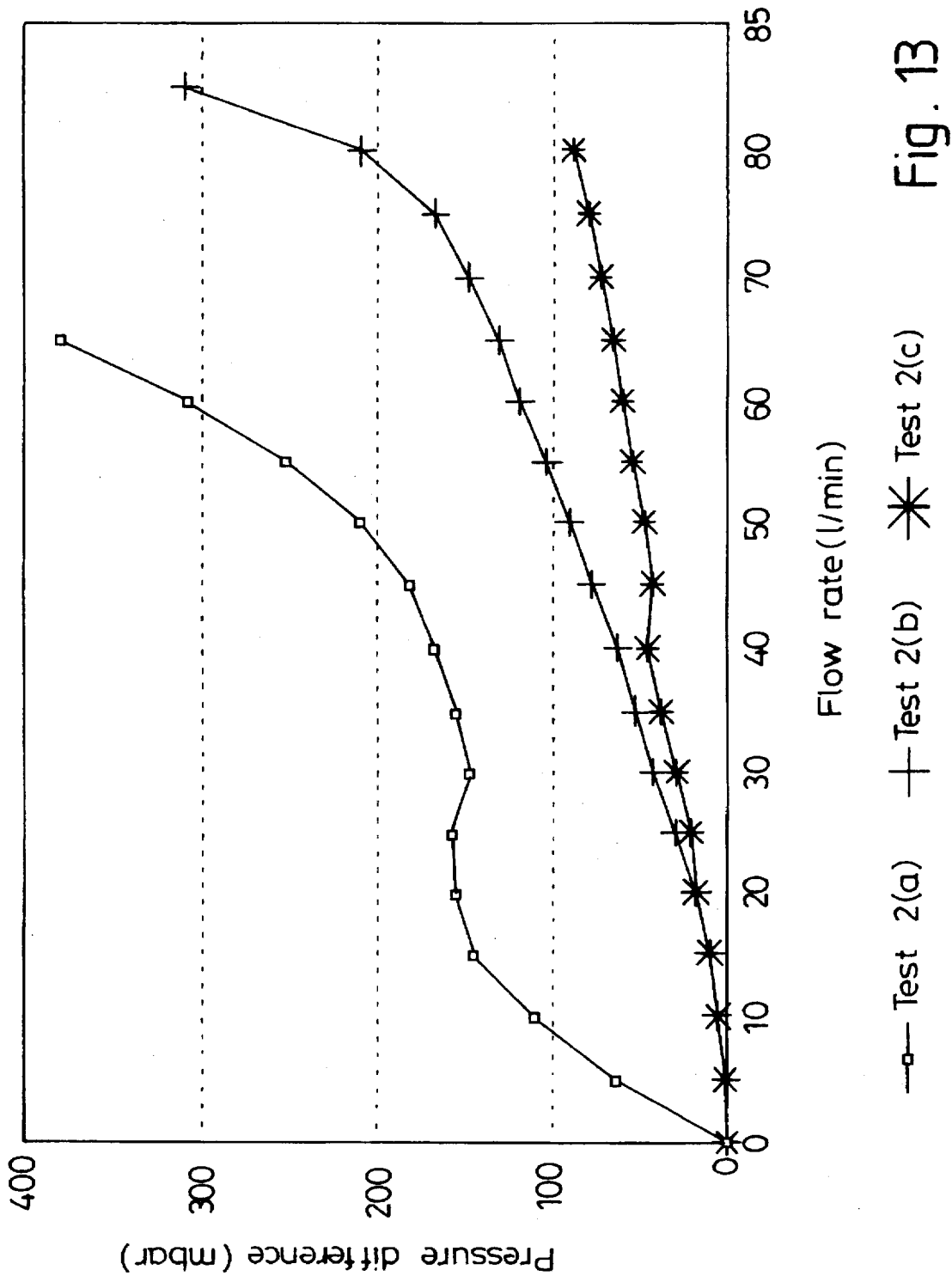
FIG. 13 shows the results of experimental tests performed on embodiments of the invention.

The characteristics of the air flow regulator portion of the device were tested by application of a vacuum. A profile of flow rate delivered against pressure drop across the portion is shown in FIG. 13.

The S-shaped profiles of tests 2(a), 2(b) and 2(c) illustrate minimum and maximum flow control characteristics of the device according to the invention.

It is to be expected that a person skilled in the art could with routine experimentation optimise the parameters above to obtain flows in response to a pressure drop within a desired range.

We claim:

1. A device for the administration of an inhalation medicament, including a body defining a through-going air pathway having a longitudinal axis, an air inlet, an air outlet forming a mouthpiece, means for dispensing medicament into the pathway and air flow regulating means which includes a movable obstructing means adapted to reduce the cross-sectional area of the pathway at a location between the air inlet and the means for dispensing medicament, and biassing means, the obstructing means being biassed into a first resting position in which the cross-sectional area of the pathway is maximum and being adapted to move against the bias of the biassing means to a second position in which the cross-sectional area of the pathway is less than maximum in response to a pressure fall at the mouthpiece caused by inhalation, wherein the air flow regulating means further includes second movable obstructing means adapted to reduce the cross-sectional area of the pathway at a location between the air inlet and the means for dispensing medicament, and second biassing means, the second obstructing means being biassed into a first resting position in which the cross-sectional area of the pathway is minimum and being adapted to move against the bias of the biassing means to a second position in which the cross-sectional area of the pathway is more than minimum in response to a pressure fall at the mouthpiece caused by inhalation.

2. A device according to claim 1 wherein the cross-sectional area of the air inlet is less than the maximum cross-sectional area of the pathway.

3. A device according to claim 1 wherein the obstructing means comprises one or more partitions adapted to slide across the pathway along an axis perpendicular to the longitudinal axis of the pathway thereby obstructing the pathway.

4. A device according to claim 1 in which the obstructing means comprises an annular segment of membrane which connects two portions of the body.

5. A device according to claim 4 in which the membrane is made of elastomeric material, and the biassing means comprises the resistance of the elastomeric material to stretching in a direction perpendicular to the longitudinal axis of the pathway.

6. A device according to claim 4 in which the obstructing means comprises an annular segment of membrane made of inelastic material and the biassing means provides a bias against movement of the two portions of the body towards each other along the longitudinal axis of the pathway.

7. A device according to claim 1 in which the obstructing means comprises a rigid grille or perforated sheet formed in a plane perpendicular to the longitudinal axis of the pathway on the air inlet side of which rests a flap which in its resting position is deflected towards the air inlet and in its second position is urged against the grille or perforated sheet.

8. A device according to claim 7 in which the flap is rigid and is hinged about an axis perpendicular to the longitudinal axis of the pathway and the biassing means comprises a spring at the hinge of the flap.

9. A device according to claim 7 in which the flap is made of a resilient elastomeric material and the biassing means consists of curvature introduced into the flap said curvature being directed towards the air inlet.

10. A device according to claim 1 in which the obstructing and biassing means together comprise two or more cooperating flaps of resilient elastomeric material which in the first position are deflected towards the air inlet and which in the second position are urged together thus reducing the cross-sectional area of the pathway.

11. A device according to claim 1 wherein the second biassing means comprises a spring biassed along the longitudinal axis of the device and wherein the second obstructing means comprises a shutter mounted on the spring.

12. A device according to claim 1 in which the cross-sectional area of the pathway when the second obstructing means is in the first position, is substantially zero.

13. A device according to claim 1, in which the biassing means comprises a spring.

14. A device according to claim 1 in which the air flow regulating means is adapted to be reversibly attached to and detached from the remainder of the device.

15. A device for the administration of an inhalation medicament, including a body defining a through-going air pathway having a longitudinal axis, an air inlet, an air outlet forming a mouthpiece, means for dispensing medicament into the pathway and air flow regulating means, wherein the air flow regulating means includes a moveable obstructing means adapted to reduce the cross-sectional area of the pathway at a location between the air inlet and the means for dispensing medicament, and biassing means, the obstructing means being biassed into a first resting position in which the cross-sectional area of the pathway is minimum and being adapted to move against the bias of the biassing means to a second position in which the cross-sectional area of the pathway is maximum in response to a pressure fall at the mouthpiece caused by inhalation and being adapted to move further to a third position in which the cross-sectional area of the pathway is less than maximum in response to a greater pressure fall at the mouthpiece caused by inhalation.

16. A device according to claim 15 in which the obstructing means is provided with an outer groove and which is retained in the housing by means of a flange within the housing around which it fits loosely.

17. A device according to claim 15 in which the obstructing means is provided with an outer flange and which is retained in the housing by means of a groove within the housing within which it fits loosely.

18. A device to claim 15 in which the biassing means and obstructing mean together comprises a perforated diaphragm made resilient elastomeric material formed in a plane perpendicular to the longitudinal axis of the pathway.

19. A device according to claim 18 in which the diaphragm is provided with one or more protrusions on its upper and lower surfaces and is located between two partitions formed in a plane perpendicular to the longitudinal axis of the pathway, the partitions being provided with apertures with which some or all of the protrusions cooperate to restrict or prevent the passage of air through the apertures.

20. A device according to claim therefor 15 in which the obstructing means is of substantially circular section along an axis perpendicular to the longitudinal axis of the pathway.

21. A device according to claim 15 in which the obstructing means comprises a V-shaped vane, biassed at a hinge formed at the apex of the V, which rotates about an axis perpendicular to that of the pathway.

22. A device according to claim 15 in which the pathway is divided by a partition provided with first aperture and the obstructing means comprises a shutter provided with a second aperture slidably engaged with the partition, which shutter is made to slide against the partition against the bias of the biassing means by a piston in gaseous communication with the mouthpiece.

23. A device according to claim therefor 15 in which the cross-sectional area of the pathway when the obstructing means is in the first position, is substantially zero.

24. A device according to claim 15 in which the biasing means comprising a spring.

25. A device according to claim 15 in which the air flow regulating means is adapted to be reversibly attached to and detached from the remainder of the device.

* * * * *